(12) United States Patent
Lee et al.

(10) Patent No.: US 7,246,517 B2
(45) Date of Patent: Jul. 24, 2007

(54) ATOMIC FORCE MICROSCOPE WITH PROBE WITH IMPROVED TIP MOVEMENT

(75) Inventors: Hak-Joo Lee, Daejeon (KR); Jae-Hyun Kim, Daejeon (KR); Chung-Seog Oh, Daejeon (KR); Seung-Woo Han, Daejeon (KR); Shin Hur, Daejeon (KR); Soon-Gyu Ko, Daejeon (KR); Byung-Ik Choi, Daejeon (KR)

(73) Assignee: Korea Institute of Machinery & Materials, Daejeon (KR)

( * ) Notice: Subject to any disclaimer, the term of this patent is extended or adjusted under 35 U.S.C. 154(b) by 0 days.

(21) Appl. No.: 11/455,353

(22) Filed: Jun. 19, 2006

(65) Prior Publication Data

US 2006/0243036 A1 Nov. 2, 2006

Related U.S. Application Data

(63) Continuation of application No. PCT/KR2004/00180, filed on Jan. 31, 2004.

(30) Foreign Application Priority Data

Jan. 5, 2004 (KR) .................... 10-2004-0000376

(51) Int. Cl.
*G01B 5/28* (2006.01)

(52) U.S. Cl. ....................................... 73/105

(58) Field of Classification Search .................... 73/105
See application file for complete search history.

(56) References Cited

U.S. PATENT DOCUMENTS

| 5,767,514 | A | * | 6/1998 | Lloyd .......................... 250/306 |
| 5,801,472 | A | * | 9/1998 | Wada et al. ................. 310/309 |
| 5,866,807 | A | | 2/1999 | Elings et al. |
| 5,869,751 | A | * | 2/1999 | Bonin ........................... 73/105 |
| 6,525,316 | B1 | * | 2/2003 | Howald ....................... 250/306 |
| 6,578,410 | B1 | * | 6/2003 | Israelachvili ................. 73/105 |

FOREIGN PATENT DOCUMENTS

| JP | 11-014641 | 1/1999 |
| JP | 2001-062791 | 3/2001 |
| JP | 2004-085220 | 3/2004 |

OTHER PUBLICATIONS

Xuefeng Wang et al. Scanning Probe Lithography Tips Sith Spring-on Tip Designs: Analysis, Fabrication, and Testing, Applied Physics Letters 87 (2005), doc 054102.*

* cited by examiner

*Primary Examiner*—Michael Cygan
(74) *Attorney, Agent, or Firm*—Knobbe Martens Olson & Bear, LLP

(57) ABSTRACT

An atomic force microscope probe provides an indentation testing function in a direction along an axis. The probe has a tip and an arm structure holding the tip. The arm structure has one end mounted on a fixed stage, the other end coupled to the AFM tip, and a hollow frame having a shape symmetric with respect to a plane including an axis on which the two ends are positioned.

21 Claims, 4 Drawing Sheets

US 7,246,517 B2

ATOMIC FORCE MICROSCOPE WITH PROBE WITH IMPROVED TIP MOVEMENT

CROSS-REFERENCE TO RELATED PATENT APPLICATIONS

This application is a continuation application under 35 U.S.C. § 365(c) of International Application No. PCT/KR2004/000180, filed Jan. 31, 2004 designating the United States. International Application No. PCT/KR2004/000180 was published in English as WO2005/066609 A1 on Jul. 21, 2005. This application further claims for the benefit of the earlier filing dates under 35 U.S.C. § 365(b) of Korean Patent Application No. 10-2004-0000376 filed Jan. 5, 2004. This application incorporates herein by reference the International Application No. PCT/KR2004/00000180 including WO2005/066609 A1 and the Korean Patent Application No. 10-2004-0000376 in their entirety.

BACKGROUND OF THE INVENTION

1. Technical Field

The present invention relates to an atomic force microscope (hereinafter, referred to as "AFM") probe, and more particularly, to an AFM cantilever having a nanoindentation testing function.

2. Description of Related Technology

Up to now, attempts to manufacture a variety of elements and parts using the nano technology have been actively made. The size of products manufactured with use of the nano technology is generally less than hundreds of nanometers. To predict mechanical properties of such products and develop design technologies, the technique for measuring mechanical properties of a test specimen whose size is less than hundreds of nanometers is required. Nanoindentation tests are very useful as methods of measuring the mechanical properties of the test specimen whose size is within a range of nanometers. Since such a nanoindentation testing function is employed in the AFM technologies that are under rapid development, attempts to measure mechanical properties such as elastic modulus and hardness of a small-sized test specimen that has never been measured even by any conventional tester can be made.

Some commercial AFM products having a nanoindentation testing function are sold. FIG. 1 schematically shows an AFM cantilever portion of the conventional AFM having an indentation testing function. The general AFM cantilever and AFM tip are made of silicon, whereas the AFM cantilever having a nanoindentation testing function is made of stainless steel and the AFM tip mounted thereon is made with diamond. One end of the AFM cantilever 10 is fixed to a fixed stage 40 and the other end of the AFM cantilever 10 becomes a free end. The AFM tip 20 is attached to a surface of the other end of the AFM cantilever 10, and a mirror 30 is mounted on the opposite surface thereof. Further, a light source (not shown) for illuminating light 70, such as laser, to the mirror 30 and a light-receiving element (not shown) for receiving light reflected from the mirror are provided to a main body of the AFM. A test specimen 60 to be measured is mounted on an xyz scanner 50 below the AFM tip 20 to be in contact with the AFM tip 20, so that the surface shape and mechanical property of the test specimen 60 are measured.

An indentation testing process for measuring the mechanical properties of the test specimen 60 using the conventional AFM shown in FIG. 1 will be described with reference to FIG. 2. When the xyz scanner 50 with the test specimen 60 mounted thereon is raised from a state "a" to a state "b" (in a z-axis direction), the AFM cantilever 10 is also displaced from a state "A to a state "B". Accordingly, a contact surface of the test specimen that is in contact with the AFM tip 20 is indented and deformed by the AFM tip 20. (On the other hand, it may be configured in such a manner that the xyz scanner 50 with the test specimen 60 mounted thereon is fixed and the fixed stage 40 with the AFM cantilever 10 fixed thereto is moved.) An amount of displacement of the AFM cantilever 10 is measured by detecting a light-receiving position of the light 70 reflected from the mirror 30 using the light-receiving element such as a photodiode, and an amount of indentation deformation of the test specimen is accordingly calculated from the difference between the amount of displacement of the AFM cantilever 10 and the amount of movement of the xyz scanner in the z-axis direction. At the moment, as shown in FIG. 2, the AFM tip is subject to a lateral motion $x_0$ as well as a vertical motion $z_0$ due to the inherent structure of the AFM cantilever 10. The general AFM is designed to measure the surface shape of the test specimen, and the lateral motion generated upon the vertical motion of the AFM cantilever is not issued. If the nanoindentation testing function is added to the conventional AFM, however, the unnecessary lateral motion in addition to the desired vertical indentation motion are generated in the AFM cantilever due to mechanical characteristics of the AFM cantilever. Therefore, the following several problems occur. That is, since the lateral motion becomes a significant error factor in the measurement of the mechanical properties of the specimen, some compensation for the lateral motion should be made such that the exact measuring results for the amount of indentation deformation of the test specimen can be obtained.

To compensate for the lateral motion, the conventional AFM may be operated as shown in FIG. 3. That is, when the test specimen 60 is subject to the lateral indentation deformation, the xyz scanner 50 is allowed to move the test specimen 60 in the horizontal direction by the amount $x_0$, so that the influence of the lateral motion can be removed. The removal of the lateral motion influence in such a manner may involve a variety of problems such as vibration occurring upon the movement of the test specimen 60, an error in the amount of movement of the test specimen, and a synchronization error between the lateral indentation motion and the test specimen movement, which in turn cause uncertainty of the measurement results to increase. In addition, the AFM cantilever of the conventional AFM is further bent on the fixed end during the indentation test. Therefore, when an indentation depth is calculated, the motion of the AFM tip positioned at the end of the cantilever should be assumed from the geometric shape of the AFM cantilever and tip. However, geometric uncertainty induced when manufacturing the AFM cantilever and tip becomes a significant error factor in the calculation of indentation depth. Since the indentation depth is a raw data that is very important in the physical property measurement, it also causes errors in the physical property measurement results. Therefore, to measure the mechanical property of the test specimen more accurately using the AFM, the aforementioned problems that may be produced in the nanoindentation test using the conventional AFM must be solved.

SUMMARY OF CERTAIN INVENTIVE ASPECTS

One aspect of the present invention provides an AFM probe capable of accurately measuring physical properties of specimens.

Another aspect of the present invention provides an AFM probe that has a nanoindentation testing function and is compatible with the conventional AFM equipment. The lateral motion generated from the conventional AFM cantilever is caused by the mechanical characteristics of the AFM cantilever.

An aspect of the present invention provides an AFM cantilever having an indentation testing function in a direction along an axis. The AFM probe comprising one end mounted on a fixed stage, the other end that is mounted with an AFM tip, and a hollow frame which takes a shape symmetric with respect to a plane including the axis on which the two ends are positioned. The AFM probe may be symmetric with respect to a plane perpendicular to the axis. The AFM cantilever may be shaped as one selected from the group consisting of a quadrangular cylinder, a circular cylinder, an elliptical cylinder, a sphere and a three-dimensional ellipse. Further, the AFM may include a mirror for reflecting light or with a displacement sensor between the two ends of the AFM probe. At this time, the displacement sensor may include a capacitance-type sensor or LVDT sensor.

DETAILED DESCRIPTION OF EMBODIMENTS

Hereinafter, embodiments of the present invention will be described in detail with reference to the accompanying drawings.

First Embodiment

Figure 4:
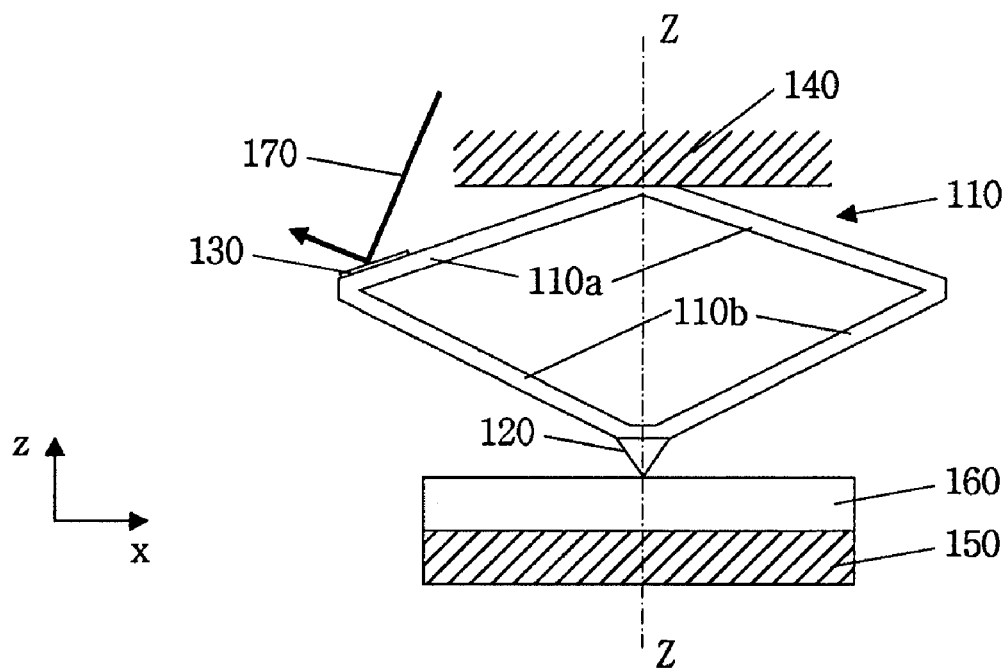
FIG. 4 is a schematic, cross-sectional view of an AFM probe having an indentation testing function according to a first embodiment of the present invention.

FIG. 4 is a schematic, cross-sectional view of an AFM probe having a nanoindentation testing function according to a first embodiment of the present invention. The AFM probe has a tip and an arm structure. The AFM probe arm structure 110 is fixedly mounted to a fixed stage 140 at an end thereof and is also mounted with an AFM tip 120 at the other end thereof, as shown in FIG. 4. In this case, the opposite ends of the AFM probe arm structure are positioned on a line Z-Z parallel to a z-axis. The AFM probe arm structure 110 takes the shape of a hollow frame symmetric with respect to the line Z-Z (more specifically, with respect to an yz plane). That is, the AFM probe arm structure 110 comprises upper arm portions 110a that extend downward in a symmetric manner with respect to the line Z-Z' divergently from the fixed stage 140, and lower arm portions 110b that further extend downward convergently from the respective ends of the upper portions 110a in a symmetric manner. A mirror 130 is mounted on one side of the left upper portion 110a of the AFM probe, which is a position where light from a light source of the AFM with the AFM probe mounted thereto is reflected to a light-receiving element of the AFM, i.e. a position corresponding to the position where the mirror 30 is mounted on the conventional AFM cantilever 10 shown in FIG. 1.

Figure 1:
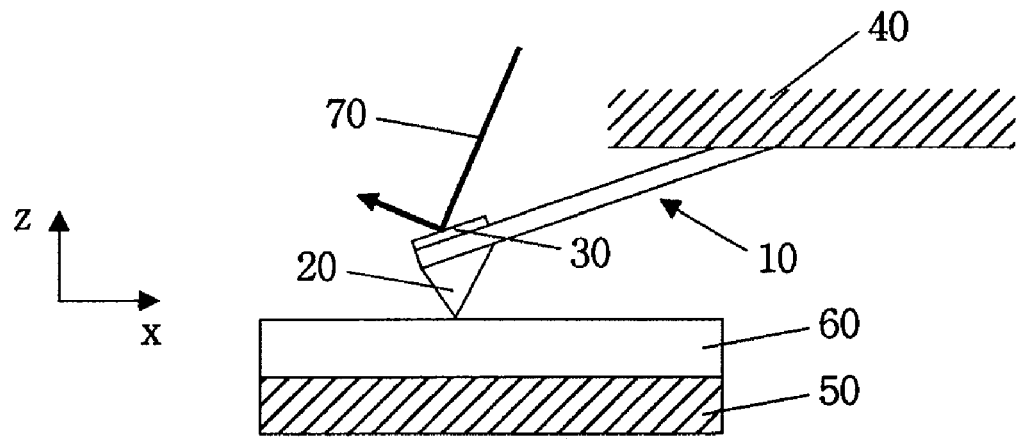
FIG. 1 is a schematic, cross-sectional view of an AFM cantilever having an indentation testing function.
Figure 2:
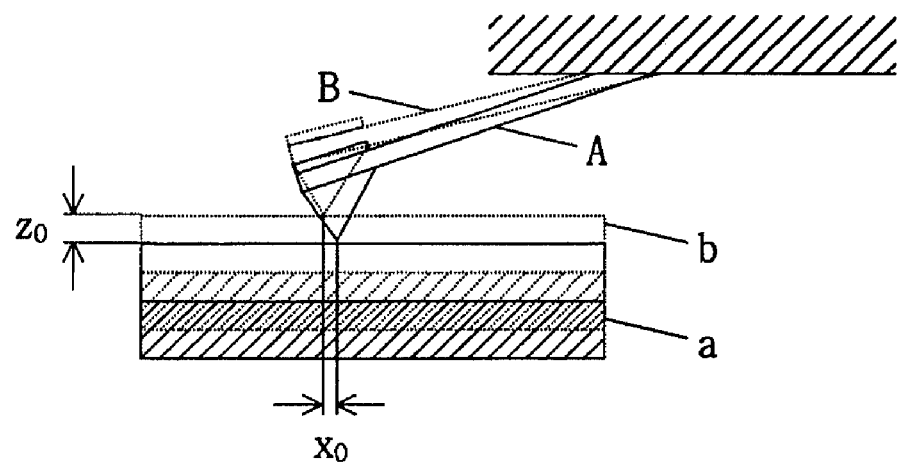
FIGS. 2 and 3 are cross-sectional views illustrating an indentation test for measuring mechanical properties of a test specimen using the conventional AFM cantilever shown in FIG. 1.
Figure 3:
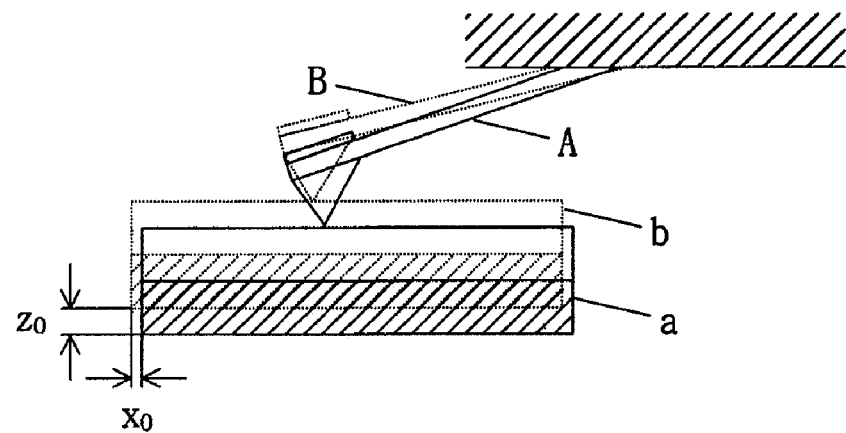
Figure 5:
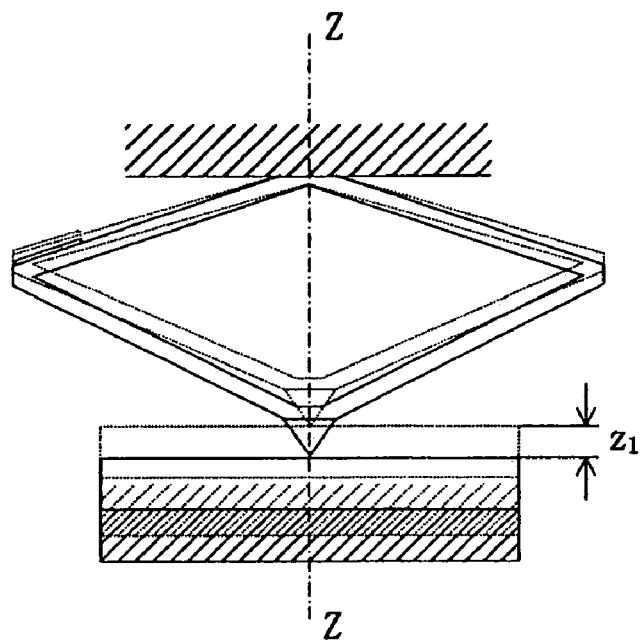
FIG. 5 is a cross-sectional view illustrating an indentation test for measuring mechanical properties of a test specimen using the AFM probe shown in FIG. 4.

As shown in FIG. 5, since the AFM probe arm structure 110 has a geometrically symmetric shape, a lateral motion (in an x-axis direction) is not produced in the AFM probe arm structure 110 during an indentation test, in which an xyz scanner 150 causes a test specimen 160 to be raised in a z-axis direction. Therefore, the AFM probe arm structure 110 of the present invention can measure an indentation depth without compensating for the lateral motion upon the calculation of the indentation depth. To measure the indentation depth, an amount of movement of an AFM tip is measured as follows. That is, the mirror 130 mounted on the one side of the upper portion 110a of the AFM probe is first installed on the same position as the mirror 30 of the conventional AFM cantilever 10 as shown in FIG. 1, and the light emitted from the light source mounted on a main body of the AFM is then caused to be reflected from the mirror, as described above with reference to FIG. 2, so that the light-receiving element installed on the main body of the AFM can receive the light reflected from the mirror. Since the AFM probe arm structure 110 of the present embodiment is elastic, the motions of the upper and lower portions 110a and 110b of the AFM probe are in linear relation. Therefore, the motion of the lower portion 110b with the AFM tip 120 mounted thereon can be calculated with a minimum error from the motion of the upper portion 110a. Since the AFM cantilever or probe is generally a consumable, the AFM cantilever is generally detachably mounted to the main body of the AFM. Therefore, the AFM probe according to this embodiment of the present invention can be mounted to and employed in the existing AFM equipment without any modifications.

The operational principle of the AFM probe arm structure 110 according to the first embodiment of the present invention will be described in more detail. Regardless of whether the AFM is used to measure a surface shape or to perform a nanoindentation test, what is important is to measure interaction between the test specimen and the AFM tip. The conventional AFM calculates the interaction between the test specimen 60 and the AFM tip 20 by measuring the displacement of the AFM cantilever 10 using laser and derives the surface shape of the test specimen on the basis of the calculated interaction. In measuring the surface shape using the AFM, quantitative values for the interaction force between the test specimen and the AFM tip and for the displacement of the AFM probe would not be important, and their relative change would be a matter of major concern. However, in the case that the nanoindentation test is performed using the AFM, the quantitative values for the interaction force between the test specimen and the AFM tip and for the displacement of the AFM probe are important. Further, the mechanical properties such as elastic modulus and hardness can be obtained using the quantitative values. Since the AFM probe arm structure 110 according to the first embodiment of the present invention shown in FIG. 5 is of a symmetric structure, only the z-axis motion is considered. The depth where the AFM tip causes the test specimen 160 to be deformed, i.e. the indentation depth, is obtained by subtracting the displacement of the AFM probe arm structure 110 from the z-axis displacement $z_1$ of the xyz scanner 150. Further, interaction force between the AFM tip 120 and the test specimen 160, i.e. indentation load, is obtained by multiplying the displacement of the AFM probe arm structure and a spring constant of the AFM probe arm structure. Although the indentation depth and load can be obtained through a similar process even in the conventional AFM cantilever, there is a problem in that some compensation for the lateral and rotational motions of the AFM cantilever are required as mentioned above. Since the displacement and load measured commonly in the AFM is very small values such as in nanometer (nm) and nanonewton (nN) unit, error factors that may be included during the compensation process exert a great influence on the measurement of physical properties.

Figure 6:
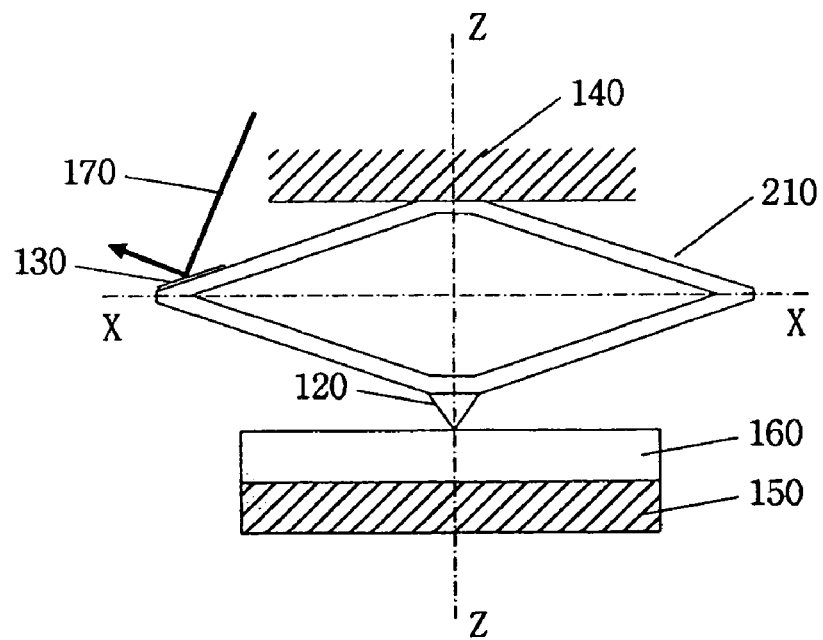
FIG. 6 is a schematic, cross-sectional view of a modified example of the AFM probe having an indentation testing function according to the first embodiment of the present invention.
Figure 7:
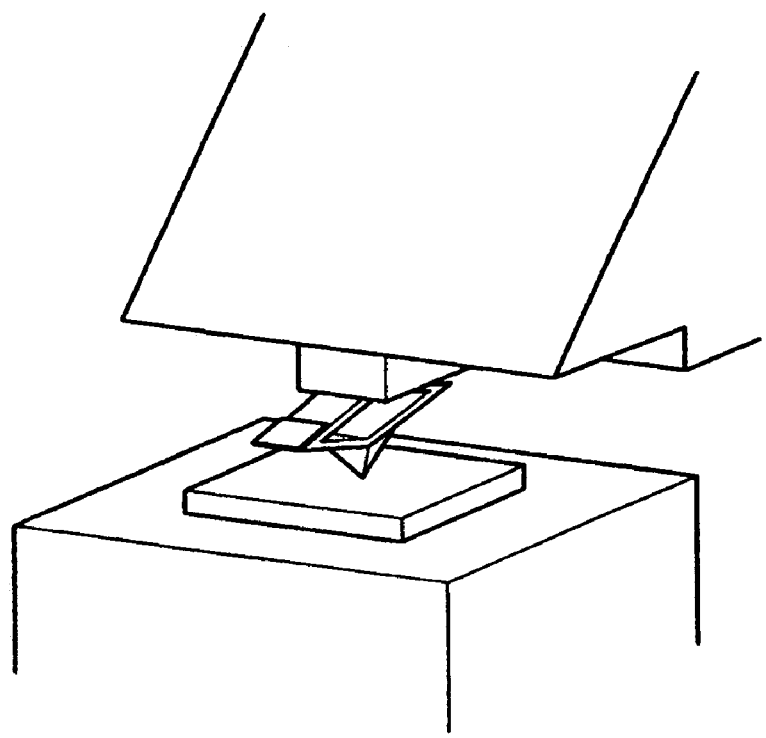
FIG. 7 is a schematic, perspective view of an AFM head to which the AFM probe having an indentation testing function according to the first embodiment of the present invention is mounted.

In the meantime, the AFM probe arm structure 110 shown in FIGS. 4 and 5 is configured to be symmetric with respect to a line X-X as well as the line Z-Z and thus to be stable, as shown in FIG. 6. In this case, the mounting position of the mirror 130 on the AFM probe arm structure 210 is the same as that of the mirror 30 on the conventional AFM cantilever 10 shown in FIG. 1, so that the AFM probe arm structure 210 of the present invention can be compatible with the conventional AFM cantilever 10. In the meantime, FIG. 7 shows a state where the AFM probe arm structure 210 of the embodiment of the present invention, which is compatible with the conventional AFM cantilever 10, is mounted on the AFM head.

In this embodiment, the AFM probe arm structure 210 may be shaped as a symmetric shape with respective to the yz plane such as a cylinder or elliptical cylinder of which cross section is a circle or ellipse, as well as a quadrangular cylinder of which cross section is a quadrangle with respect to the xz plane as shown in FIGS. 4 through 7. A three-dimensional shape such as a hollow sphere or three-dimensional ellipse may also be employed.

Second Embodiment

The displacement of the AFM probe same as in the aforementioned first embodiment may be measured using laser light. Such a method is widely used in the conventional AFM cantilever, but it causes the structure of the AFM to be complicated. Further, there may be an inconvenience in that the AFM cantilever or probe should be manually manipulated such that the laser light can be incident upon the mirrors 30 and 130 thereof whenever the AFM cantilever 10 and probe arm structure 110, and 210 are exchanged from the AFM head. In the second embodiment, a displacement sensor 330 capable of measuring the displacement of the AFM probe without using the light source and the light receiving element (not shown) is employed in the AFM probe arm structure 310 shown in FIG. 8.

Figure 8:
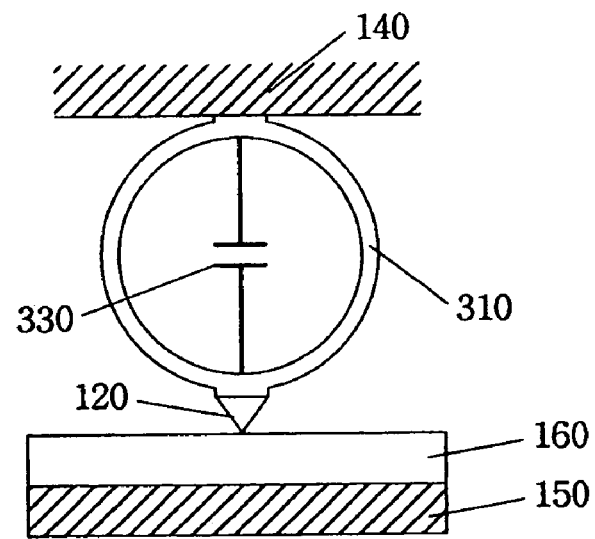
FIG. 8 is a schematic, cross-sectional view of an AFM probe having an indentation testing function according to a second embodiment of the present invention.

In the second embodiment, the AFM probe arm structure 310 uses a circular frame. As shown in FIG. 8, the displacement sensor 330 is mounted in the z-axis direction in the circular AFM probe arm structure 310 symmetric with respect to the x and z axes, and more specifically, between one end of the AFM cantilever fixed to the fixed stage 140 and the other end on which the AFM tip 120 is mounted. The displacement sensor 330 is a non-contact sensor with sufficient resolution. For example, a capacitance-type sensor or LVDT (Linear Variable Differential Transformer) sensor may be used as the displacement sensor 330. The AFM probe arm structure 310 can measure the indentation depth by subtracting a displacement value measured by the displacement sensor 330 from a displacement value of the xyz scanner 150. In addition, the indentation load can be obtained by multiplying a displacement value measured from the displacement sensor 330 by a stiffness value of the AFM probe arm structure 310.

Although the AFM probe arm structure 310 according to the second embodiment of the present invention is configured to include the circular frame, either a shape shown in FIG. 4 or FIG. 6 or an elliptical shape may be used in this AFM cantilever as described above, and a hollow spherical frame (axisymmetric shape) may also be used in this cantilever. In a case where the axisymmetric spherical frame is used, it can be configured in such a manner that a hemisphere to be attached to the fixed stage 140 and another hemisphere to be attached to the AFM tip are separately manufactured, the capacitance-type sensor is installed therein and the hemispheres are then bonded to each other.

In the present invention including the first and the second embodiments, the AFM cantilever is mounted with the AFM tip or on the fixed stage, and thus, it cannot be geometrically shaped as an exact quadrangular cylinder, circular cylinder, elliptical cylinder, sphere or three-dimensional ellipse. Accordingly, the shapes of the quadrangular cylinder, circular cylinder, elliptical cylinder, sphere or three-dimensional ellipse as used herein cannot mean an exact geometric shape but a general shape as a whole. Further, it is obvious to those skilled in the art that the symmetry of the AFM cantilever with respect to the yz plane according to the present invention does not mean the mathematically exact symmetry but the symmetry sufficient to prevent unnecessary x-axis motions from occurring when the AFM cantilever is subjected to the indentation deformation in the z-axis direction.

The present invention makes it possible to measure more exact physical properties of the interaction between the AFM tip and the test specimen by solving the problem from the lateral motion inevitably involved in the conventional AFM cantilever. The present invention is very advantageous in allowing the AFM to have the nanoindentation testing function and can also be used directly in the measurement for the various surface shapes corresponding to a unique function of the AFM as well as the AFM nano indentation test. Further, the AFM cantilever according to the first embodiment of the present invention can be mounted with replacement of the conventional AFM cantilever in a compatible mode to the conventional AFM equipment, without any modification of the conventional AFM equipment.

Although the present invention has been described in connection with the embodiments thereof, it will be apparent to those skilled in the art that various changes and modifications can be made thereto without departing from the scope and spirit of the present invention defined by the appended claims. Therefore, simple changes of the embodiments of the present invention will fall within the scope of the invention.

What is claimed is:

1. An apparatus comprising an atomic force microscope probe, which comprises:
   a scanning tip configured to scan a surface of a sample; and
   an arm structure configured to suspend the scanning tip over a sample to be scanned, wherein the arm structure has a first point and a second point, which define a first axis passing the first and second points, and wherein the arm structure is configured to allow the scanning tip to move relative to the first point along the first axis without substantial movement relative to the first point along a second axis perpendicular to the first axis.

2. The apparatus of claim 1, wherein the arm structure comprises a first arm and a second arm diverging from each other at a first position of the arm structure and converging at a second position of the arm structure, and wherein at least one of the first and second arms comprises a portion configured to move relative to the first point along the first axis.

3. The apparatus of claim 2, wherein at least one of the first and second arms comprises two substantially straight arm portion, wherein one end of each arm portion is joined at the first or second position of the arm structure, and wherein the two arm portions are joined together at the other end thereof.

4. The apparatus of claim 2, wherein at least one of the first and second arms comprises a curved arm portion, and wherein the curved arm portion is substantially pliable such that the first and second positions are movable relative to each other along the first axis.

5. The apparatus of claim 2, wherein the first and second positions are on the first axis.

6. The apparatus of claim 2, wherein the first and second arms are substantially symmetrical with respect to a plane, on which the first axis passes.

7. The apparatus of claim 2, wherein the first position is apart from the second position at a distance, and wherein the arm structure is configured such that the distance changes as the scanning tip scans the surface.

8. The apparatus of claim 2, wherein the probe further comprises a displacement sensor configured to monitor changes of the distance between the first and second positions.

9. The apparatus of claim 1, wherein the apparatus comprises a probe cartridge for use in an atomic force microscope.

10. The apparatus of claim 1, wherein the apparatus comprises an atomic force microscope.

11. The apparatus of claim 1, wherein the arm structure comprises an arm comprising the first point, the second point and a third point, wherein the first and second points are positioned on and movable relative to each other along the first axis, and wherein the third point is movable along at least the second axis.

12. An apparatus comprising an atomic force microscope probe, the apparatus comprising:
    a scanning tip configured to scan a surface of a sample; and
    an arm structure configured to suspend the scanning tip over a sample to be scanned, the arm structure comprising a first arm and a second arm, which diverge from each other at a first position of the arm structure and converge at a second position of the arm structure, wherein the scanning tip is configured to move relative to the first position along an axis passing the first and second positions as the scanning tip scans the surface.

13. The apparatus of claim 12, wherein the first position is apart from the second position at a distance, which is adapted to vary as the scanning tip scans the surface.

14. The apparatus of claim 12, wherein the arm structure is configured such that the scanning tip does not substantially move relative to the first position in a direction substantially perpendicular to the axis as the scanning tip scans the surface.

15. An apparatus comprising an atomic force microscope probe, the apparatus comprising:
    a scanning tip configured to scan a surface of a sample; and
    means for suspending the scanning tip over the surface, wherein the suspending means has first and second points, which define a first axis passing the first and second points, and wherein the suspending means allows movement of the scanning tip relative to the first point along the first axis and substantially prevents movement relative to the first point along a second axis perpendicular to the first axis.

16. A method of probing a sample using an atomic force microscope, the method comprising:
    providing an atomic force microscope comprising a probe and a probe receiver configured to receive the probe, the probe comprising a tip and an arm structure suspending the tip, wherein the arm structure has a first point and a second point, which define a first axis passing the first and second points;
    placing the probe over a sample; and
    scanning the sample while moving the sample relative to the probe in a direction, wherein the tip moves relative to the first point along the first axis while scanning does not cause substantial movement of the tip relative to the first point along a second axis perpendicular to the first axis.

17. The method of claim 16, wherein the arm structure is configured to allow the tip to move relative to the first point along the first axis without substantial movement relative to the first point of the tip along the second axis.

18. The method of claim 16, wherein the arm structure comprises a first arm and a second arm diverging from each other at a first position of the arm structure and converging at a second position of the arm structure, and wherein at least one of the first and second arms comprises a portion configured to move relative to the first point along at least one of the first and second axes.

19. The method of claim 18, further comprising monitoring changes of the distance between the first and second positions of the arm structure.

20. The method of claim 16, further comprising monitoring the movement of the tip relative to the first point along the first axis.

21. The method of claim 16, wherein providing the atomic force microscope comprises providing an atomic force microscope, in which the probe comprises a cantilever, which can move along both the first and second axes while scanning a surface, and wherein providing the atomic force microscope further comprises replacing the probe comprising the cantilever with the probe comprising the arm structure, which is configured to substantially avoid movement of the tip relative to the first point along the second axis.

* * * * *

UNITED STATES PATENT AND TRADEMARK OFFICE
CERTIFICATE OF CORRECTION

PATENT NO. : 7,246,517 B2 Page 1 of 1
APPLICATION NO. : 11/455353
DATED : July 24, 2007
INVENTOR(S) : Lee et al.

It is certified that error appears in the above-identified patent and that said Letters Patent is hereby corrected as shown below:

On the title page, item (63), (Related U.S. Application Data), in line 1, please delete "PCT/KR2004/00180" and insert -- PCT/KR2004/000180 --.

On the title page, item (56), column 2 (Other Publication), in line 1-2, please delete "Spring-on Tip" and insert -- Spring-on-Tip --.

In column 2, line 7, please replace "a state "A to" with -- a state "A" to --.

Signed and Sealed this

Eighth Day of July, 2008

JON W. DUDAS
*Director of the United States Patent and Trademark Office*